United States Patent [19]

Heubach et al.

[11] Patent Number: 4,639,266
[45] Date of Patent: Jan. 27, 1987

[54] PLANT PROTECTION AGENTS BASED ON 1,2,4-TRIAZOLE DERIVATIVES AND ALSO NEW DERIVATIVES OF 1,2,4-TRIAZOLE

[75] Inventors: Günther Heubach, Kelkheim; Klaus Bauer, Rodgau; Hermann Bieringer, Eppstein, all of Fed. Rep. of Germany

[73] Assignee: Hoechst Aktiengesellschaft, Frankfurt, Fed. Rep. of Germany

[21] Appl. No.: 774,067

[22] Filed: Sep. 9, 1985

[30] Foreign Application Priority Data

Sep. 11, 1984 [DE] Fed. Rep. of Germany ....... 3433249
Jul. 15, 1985 [DE] Fed. Rep. of Germany ....... 3525205

[51] Int. Cl.[4] .................. A01N 43/653; A01N 43/84; C07D 294/08
[52] U.S. Cl. ......................... 71/92; 548/262; 548/237; 546/199; 544/139; 71/88; 71/90; 71/94; 71/98; 71/100; 71/106; 71/108; 71/118
[58] Field of Search ................ 548/262, 237; 546/199; 544/132; 71/92

[56] References Cited

FOREIGN PATENT DOCUMENTS 0031938 12/1980 European Pat. Off. ............... 71/92
1123331 2/1962 Fed. Rep. of Germany ...... 548/262
51/88968 8/1976 Japan .................................. 548/262

OTHER PUBLICATIONS

Hellmann et al., "Chem. Ber.", vol. 94, pp. 1868–1870 (1961).
Regitz et al., "Chem. Ber.", vol. 96, pp. 3120–3132 (1963).
Ruccia et al., "Ann. Chim. (Rome)," vol. 57, No. 6, pp. 671–679 (1967).

Primary Examiner—Robert T. Bond
Attorney, Agent, or Firm—Curtis, Morris & Safford

[57] ABSTRACT

The invention relates to plant protection agents which contain a triazole compound of the formula I

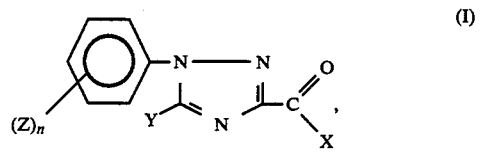

in which Z denotes halogen, nitro, cyano, trifluoromethyl, (substituted) alkyl, (substituted) alkoxy, (substituted) alkylthio, (substituted) cycloalkyl, (substituted) phenyl or (substituted) phenoxy, Y denotes H, (substituted) alkyl, alkenyl, alkinyl or (substituted) cycloalkyl, X denotes hydroxyl, alkyl, cycloalkoxy, phenoxy, alkenyloxy, alkinyloxy, (substituted) alkoxy, (substituted) alkylthio or a radical of the formulae

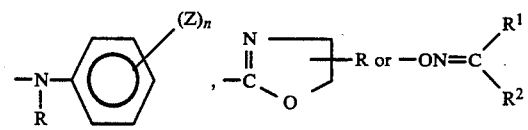

and n denotes 0, 1, 2 or 3, and salts thereof, and to new compounds of the formula I as defined above, Y denoting $CCl_3$ or $CHCl_2$ in the event that X denotes ($C_1$–$C_4$)-alkyl, and compounds in which (a) Y denotes H, $(Z)_n$ denotes H, 4-Cl, 4-$CH_3$, 2-$OCH_3$, 4-$OCH_3$ or 4-$OC_2H_5$ and X denotes OH, $OCH_3$ or $OC_2H_5$,
(b) Y denotes $CH_3$, $(Z)_n$ denotes 4-$NO_2$, 4-$OCH_3$, 2-Cl, 4-Cl, 2-$OCH_3$-4-$NO_2$ or 2-$CH_3$-4-$NO_2$ and X denotes OH or $OC_2H_5$ and
(c) Y denotes $C_2H_5$ or $CH(CH_3)_2$, $(Z)_n$ denotes H and X denotes $OCH_3$ being excepted. The compounds of the formula I are suitable for protecting crop plants from the phytotoxic side-effects of plant protection agents.

7 Claims, No Drawings

PLANT PROTECTION AGENTS BASED ON 1,2,4-TRIAZOLE DERIVATIVES AND ALSO NEW DERIVATIVES OF 1,2,4-TRIAZOLE

The present invention relates to plant protection agents containing a triazole compound of the formula I

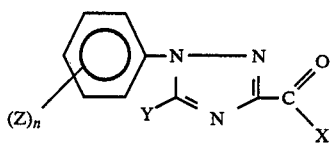

in which
the Zs are identical or different and denote halogen, nitro, cyano, trifluoromethyl, $(C_1-C_4)$-alkyl, $(C_1-C_4)$-alkoxy or $(C_1-C_4)$-alkylthio, it being possible for the alkyl, alkoxy and alkylthio groups to be substituted by one or more halogen atoms, in particular fluorine or chlorine, or $(C_3-C_6)$-cycloalkyl which can be substituted by $(C_1-C_4)$-alkyl, or denotes phenyl or phenoxy, it being possible for phenyl and phenoxy to be monosubstituted or polysubstituted by halogen and/or monosubstituted by trifluoromethyl, Y denotes hydrogen, $(C_1-C_4)$-alkyl which can be wholly or partially substituted by halogen atoms and/or monosubstituted by $(C_1-C_4)$-alkoxy or $(C_1-C_4)$-alkylthio, or $(C_2-C_6)$-alkenyl or $(C_2-C_6)$-alkinyl or denotes $((C_3-C_6)$-cycloalkyl which can be substituted by $(C_1-C_4)$-alkyl and/or a dichlorovinyl radical, and X denotes hydroxyl, $(C_1-C_4)$-alkyl, $((C_3-C_6)$-cycloalkoxy, phenyl-$(C_1-C_6)$-alkoxy, phenoxy, $(C_2-C_6)$-alkenyloxy, $(C_2-C_6)$-alkinyloxy or $(C_1-C_6)$-alkoxy or $(C_1-C_6)$-alkyl-thio, it being possible for the alkoxy or alkylthio group to be substituted by $(C_1-C_2)$-alkoxy, mono-$(C_1-C_4)$-alkylaminocarbonyl, di-[$(C_1-C_4)$-alkyl]aminocarbonyl, phenylaminocarbonyl, N-[$(C_1-C_4$ alkyl]-N-phenyaminocarbonyl, mono-$(C_1-C_6)$-alkylamino, di-$(C_1-C_6$ -alkylamino, $(C_1-C_6$ -alky)carbonyloxy, $(C_1-C_2)$-alkylthio, cyano or halogen, or denotes a radical of the formulae

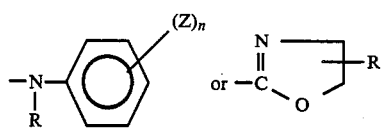

in which R in each case denotes hydrogen or $(C_1-C_4)$-alkyl, or denotes mono-$(C_1-C_4)$-alkylamino, di-$(C_1-C_4)$-alkylamino, $(C_5-C_6)$-cycloalkylamino, piperidino, morpholino or 2,6-dimethylmorpholino or a radical of the formula

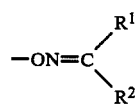

in which $R^1$ and $R^2$ can be identical or different and denote $(C_1-C_4)$-alkyl radicals, and in which $R^1$ and $R^2$ together can also form a 5-membered, 6-membered or 7-membered cycloalkyl radical, and n denotes the number 0, 1, 2 or 3, or, in the event that X=OH, salts thereof which can be employed for agriculture.

Examples of suitable salts are metal salts, such as alkali or alkaline earth metal salts, in particular sodium or potassium salts or salts with ammonium, mono-, di-, tri- or tetra-$(C_1-C_4)$-alkylammonium or with mono-, di-, tri- or tetra-$(C_1-C_4)$-alkanolammonium.

Preferred compounds of the formula I are those in which Y denotes $(C_1-C_2)$-alkyl which can be wholly or partially substituted by F, Cl or Br,
the Zs are identical or different and denote halogen, $(C_1-C_4)$-alkoxy, $(C_1-C_4)$-alkyl or $CF_3$ and
X denotes $(C_1-C_6)$-alkoxy or hydroxyl and
n denotes 1, 2 or 3.

Particularly preferred representatives of these compounds are those in which Y denotes $CCL_3$, $CHCL_2$, $CHF_2CF_2$ or $CH_3$.

Surprisingly, these compounds of the formula I are suitable for effectively reducing or entirely eliminating the phytotoxic side-effects of plant protection agents in crop plants. Compounds of this type are also known as antidotes or safeners.

Some of the compounds of the formula I are known from scientific publications (Chem. Ber. 94 1868 (1961), Chem. Ber. 96 3210 (1963) and Chem. Ber. 98 642 (1965)) and from German Pat. No. 1,123,321. Their safener action had, however, not been discovered.

The present invention also relates to the compounds of the formula I which are new, that is to say have not been described before. These are the compounds of the formula I

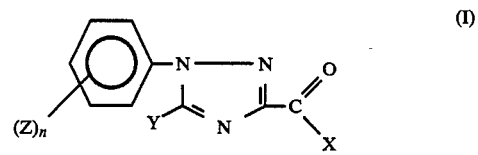

in which
the Zs are identical or different and denote halogen, nitro, cyano, trifluoromethyl, $(C_1-C_4)$-alkyl, $(C_1-C_4)$-alkoxy or $(C_1-C_4)$-alkylthio, it being possible for the alkyl, alkoxy and alkylthio groups to be substituted by one or more halogen atoms, in particular fluorine or chlorine, or $(C_3-C_6)$-cycloalkyl which can be substituted by $(C_1-C_4)$-alkyl, or denotes phenyl or phenoxy, it being possible for phenyl and phenoxy to be monosubstituted or polysubstituted by halogen and/or monosubstituted by trifluoromethyl, Y denotes hydrogen, $(C_1-C_4)$-alkyl which can be wholly or partially substituted by halogen atoms and/or monosubstituted by $(C_1-C_4)$-alkoxy or $(C_1-C_4)$-alkylthio, or $(C_2-C_6)$-alkenyl or $(C_2-C_6)$-alkinyl or denotes $(C_3-C_6)$-cycloalkyl which can be substituted by $(C_1-C_4)$-alkyl and/or a dichlorovinyl radical, and X denotes hydroxyl, $(C_1-C_4)$-alkyl, $((C_3-C_6)$-cycloalkoxy, phenyl-$(C_1-C_6)$-alkoxy, phenoxy, $(C_2-C_6)$-alkenyloxy, $(C_2-C_6)$-alkinyloxy or $(C_1-C_6)$-alkoxy or $(C_1-C_6)$-alkylthio, it being possible for the alkoxy or alkylthio group to be substituted by $(C_1-C_2)$-alkoxy, mono-$(C_1-C_4)$- alkylaminocarbonyl, di-[($C_1$-$C_4$)-alkyl]aminocarbonyl, phenylaminocarbonyl, N-[($C_1$-$C_4$)-alkyl]-N-pheny-aminocarbonyl, mono-($C_1$-$C_6$)-alkylamino, di-($C_1$-$C_6$)-alkylamino, ($C_1$-$C_6$-alkylcarbonyloxy, ($C_1$-$C_2$)-alkylthio, cyano or halogen, or denotes a radical of the formulae

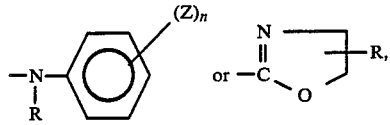

in which R in each case denotes hydrogen or ($C_1$-$C_4$)-alkyl, or denotes mono-($C_1$-$C_4$)-alkylamino, di-($C_1$-$C_4$)-alkylamino, ($C_5$-$C_6$)-cycloalkylamino, piperidino, morpholino or 2,6-dimethylmorpholino or a radical of the formula

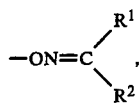

in which $R^1$ and $R^2$ can be identical or different and denote ($C_1$-$C_4$)-alkyl radicals, and in which $R^1$ and $R^2$ together can also form a 5-membered, 6-membered or 7-membered cycloalkyl radical, and n denotes the number 0, 1, 2 or 3, or, in the event that X=OH, salts thereof which can be employed for agriculture, it being necessary, in the event that X=($C_1$-$C_4$)-alkyl for Y to denote $CCL_3$ or $CHCL_2$, and excepting the compounds of the formula I in which (a) Y denotes H, $(Z)_n$ denotes H, 4-Cl, 4-$CH_3$, 2-$OCH_3$, 4-$OCH_3$ or 4-$OC_2H_5$ and X denotes OH, $OCH_3$ or $OC_2H_5$, (b) Y denotes $CH_3$, $(Z)_n$ denotes 4-$NO_2$, 4-$OCH_3$, 2-CL, 4-CL, 2-$OCH_3$-4-$NO_2$ or 2-$CH_3$-4-$NO_2$ and X denotes OH or $OC_2H_5$ and (c) Y denotes $C_2H_5$ or $CH(CH_3)_2$, $(Z)_n$ denotes H and X denotes $OCH_3$.

The present invention also relates to a process for the preparation of the new compounds of the formula I and salts thereof, which comprises reacting (a) a compound of the formula II

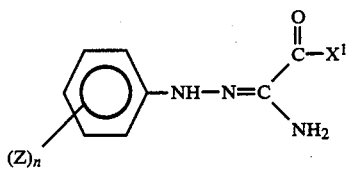

in which $X^1$ has the meaning of X with the exception of hydroxyl, ($a_1$) with a compound of the formula Y-CO-Cl or ($a_2$) with an acid anhydride of the formula Y-CO-O-CO-Y or ($a_3$) with an orthoester of the formula Y-C($OR^1$)$_3$ in which $R^1$ denotes ($C_1$-$C_4$)-alkyl, or (b) in the case of compounds in which Y=H or ($C_1$-$C_4$)-alkyl, reacting a compound of the formula III

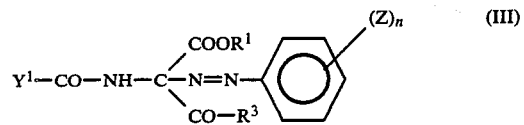

in which $Y^1$ denotes H or ($C_1$-$C_4$)-alkyl and $R^3$ denotes ($C_1$-$C_4$)-alkoxy or $CH_3$, with a base, the compounds obtained under ($a_1$) and ($a_2$) being heated, if appropriate, in acetic acid, and the resulting compounds of the formula I being converted, if appropriate, into other compounds of the formula I or salts thereof by the formation of derivatives.

It is surprising in process variants ($a_1$) and ($a_2$) that, as well as the addition of the acid chloride or anhydride to the free amino group, direct cyclization to give the compounds of the formula I is frequently observed immediately subsequently in a two-stage reaction. It is also surprising that, in the case of ($a_1$), the reaction takes place without the addition of a base. On the contrary, the addition of bases, which is otherwise customary, results in resinous products.

The reactions of the compounds of the formula II with a carboxylic acid chloride (YCOCl), acid anhydride or orthoester are advantageously carried out in an organic, inert, proton-free solvent. In the case of the acid anhydride or orthoester (variant $a_2$ or $a_3$), the reagent concerned can itself also be used as the solvent. Process variant ($a_3$) can be carried out advantageously in the presence of an acid catalyst, in particular an organic acid, such as p-toluenesulfonic acid.

Suitable inert solvents for process variants ($a_1$), ($a_2$) and ($a_3$) are, in particular, aromatic compounds, such as benzene, toluene, xylene or chlorobenzene or cyclic ether compounds, such as tetrahydrofuran or dioxane, or ketones, such as acetone, and dipolar, aprotic solvents, such as dimethylformamide. Depending on the solvent, the reaction temperatures vary between 10° C. and the boiling point of the reaction mixture. If aromatic solvents are employed in the case of variant ($a_1$), after the carboxylic acid chloride has been added, the water formed is removed under reflux by means of a water separator. In the case of the process variants ($a_1$) or ($a_2$), depending on the radical $(Z)_n$ and X in the compounds of the formula II, an intermediate product of the formula IV

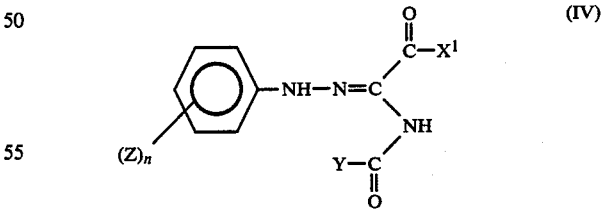

which can be isolated under certain circumstances, is formed initially in several cases. If the reaction stops at this stage when the abovementioned solvents are used, a subsequent reaction in acetic acid must be carried out. This is effected by heating the intermediate product of the formula IV in acetic acid at between approx. 50° C. and reflux temperature. This subsequent reaction can be carried out in a one-pot process, the organic solvent of the first process stage being removed by distillation before the acetic acid is added.

Process variant (b) for the preparation of the compounds of the formula I is known in principle in accordance with Chem. Ber. 96 3120 (1963). The bases employed are, in particular, inorganic bases, preferably sodium hydroxide or potassium hydroxide. The preparation of the compounds of the formula III is effected, as described in the reference, by reacting acetamidomalonic ester or acetaminoacetoacetic ester compounds with diazonium salts.

The compounds of the formula I thus obtained can be converted into other compounds of the formula I by customary reactions for the formation of derivatives. Thus the compounds of the formula I in which X=OH can be obtained from the ester compounds of the formula I by acid or alkaline hydrolysis. The salts of the compounds of the formula I can be obtained by a customary route from the acids of the formula I (X=OH) by adding appropriate bases. Other esters or amides of the formula I can also be obtained from the ester compounds of the formula I in a customary manner, for example via the corresponding acid chlorides.

The preparation of compounds of the formula II is known in principle; the compounds of the formula II can be prepared by reacting α-chlorohydrazones of the formula V

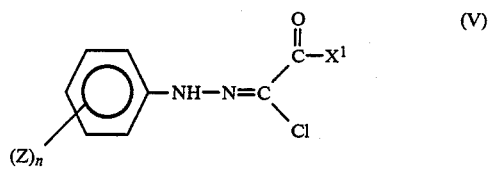

with ammonia. The compounds of the formula V are accessible in turn by reacting phenyldiazonium salts with α-halogenoacetoacetic esters or α-halogeno-β-diketones. The two reactions are described in J. Chem. Soc. 87 1859 (1905) and Ber. d. dt. Chem. Ges. 50 1482 (1917).

The compounds of the formula I are primarily suitable for protecting crop plants from the toxic side-effects of herbicides.

The compounds of the formula I can be applied together with other herbicides, and are then capable of antagonizing or completely eliminating the harmful side-effects of these herbicides, without impairing the herbicidal effectiveness of these herbicides against weeds. This makes it possible to enlarge the field of use of conventional plant protection agents quite considerably.

Safeners for herbicides of the type of phenoxyphenoxycarboxylic acid esters are known from published European Application No. 31,938. These safeners, however, have an inadequate action.

Examples of herbicides exerting phytotoxic side-effects which can be reduced by means of the compounds of the formula I are carbamates, thiolcarbamates, halogenoacetanilides, substituted phenoxycarboxylic, naphthoxycarboxylic and phenoxyphenoxycarboxylic acid derivatives and also heteroaryloxyphenoxycarboxylic acid derivatives, such as quinolyloxy-, quinoxalyloxy-, pyridyloxy-, benzoxazolyloxy- and benzthiazolyloxy-phenoxycarboxylic acid esters and also dimedoneoxime derivatives. Of these, phenoxyphenoxycarboxylic and heteroaryloxyphenoxycarboxylic acid esters are preferred. Esters which are particularly suitable in this connection are lower alkyl, alkenyl and alkinyl esters.

The following herbicides may be mentioned as examples, without intending thereby to express a limitation:

(A) herbicides of the type of the ($C_1$–$C_4$)-alkyl, ($C_2$–$C_4$)-alkenyl and ($C_3$–$C_4$)-alkinylphenoxyphenoxycarboxylates and heteroaryloxyphenoxycarboxylates, such as methyl 2-(4-(2,4-dichlorophenoxy)-phenoxy)-propionate, methyl 2-(4-(4-bromo-2-chlorophenoxy)-phenoxy)-propionate, methyl 2-(4-(4-trifluoromethylphenoxy)-phenoxy)-propionate, methyl 2-(4-(2-chloro-4-trifluoromethylphenoxy)-phenoxy)propionate, methyl 2-(4-(2,4-dichlorobenzyl)-phenoxy)-propionate, ethyl 4-(4-(4-trifluoromethylphenoxy)-phenoxy)-pent-2-ene, ethyl 2-(4-(3,5-dichloropyrid-2-yloxy)-phenoxy)-propionate, propargyl 2-(4-(3,5-dichloropyrid-2-yloxy)-phenoxy)-propionate, ethyl 2-(4-(6-chlorobenzoxazol-2-yloxy)-phenoxy)-propionate, ethyl 2-(4-(6-chlorobenzthiazol-2-yloxy)-phenoxy)-propionate, methyl 2-(4-(3-chloro-5-trifluoromethyl-2-pyridyloxy)-phenoxy)-propionate, butyl 2-(4-(5-trifluoromethyl-2-pyridyloxy)-phenoxy)-propionate, ethyl 2-(4-(6-chloro-2-quinoxalyloxy)-phenoxy)-propionate, ethyl 2-(4-(6-fluoro-2-quinoxalyloxy)-phenoxy)-propionate and ethyl 2-(4-(6-chloro-2-quinolyloxy)-phenoxy)-propionate, (B) chloroacetanilide herbicides, such as N-methoxymethyl-2,6-diethylchloroacetanilide, N-(3'-methoxyprop-2'-yl)-methyl-6-ethyl-chloroacetanilide and N-(3-methyl-1,2,4-oxdiazol-5-ylmethyl)-chloroacetic acid 2,6-dimethylanilide, (C) thiocarbamates, such as S-ethyl N,N-dipropylthiocarbamate or S-ethyl N,N-diisobutylthiocarbamate (D) dimedone derivatives, such as 2-(N-ethoxybutyrimidoyl)-5-(2-ethylthiopropyl)-3-hydroxy-2-cyclohexen-1-one, 2-(N-ethoxybutyrimidoyl)-5-(2-phenylthiopropyl)-3-hydroxy-2-cyclohexen-1-one or 2-(1-allyloxyiminobutyl)-4-methoxycarbonyl-5,5-dimethyl-3-oxocyclohexenol.

The safener:herbicide ratio can vary within wide limits, within the range between 1:10 and 10:1, in particular between 2:1 and 1:10. The optimum amounts of herbicide and safener in a particular case depend on the type of herbicide used or on the safener used and on the nature of the plant crop to be treated, and can be determined on a case by case basis by appropriate tests.

The principal fields of use for the application of the safeners are, above all, cereal crops (wheat, rye, barley or oats), rice, maize, sorghum and also cotton, sugar beet, sugar cane and soya beans.

Depending on their properties, the safeners of the formula I can be used for pretreating the seed of the crop plant (seed dressing), or can be introduced into the seed furrows before sowing or can be used together with the herbicide before or after the emergence of the plants. Pre-emergence treatment includes both treatment of the cultivated area before sowing and treatment of cultivated areas which have been sown but are not yet covered with vegetation. Conjoint use together with the herbicide is preferred. Tank mixtures or finished formulations can be employed for this purpose.

The present invention also relates, therefore, to a process for protecting crop plants from the phytotoxic side-effects of herbicides, which comprises applying an effective amount of a compound of the formula I before, after or at the same time as the herbicide.

The compounds of the formula I also display fungicidal effects and can, therefore, be employed for combating phytopathogenic fungi, such as, for example, powdery mildew fungi, rust fungi and fungi of the genera Phytopthora, Botrytis, Piricularia or *Venturia inequalis*. For application, the compounds of the formula I can be formulated together with customary formulation auxiliaries to give dusting agents, wettable powders, dispersions, emulsion concentrates and the like, which can either be applied as such (dusting agents or pellets) or can be dissolved or dispersed in a solvent (water) before application.

In addition, the compounds of the formula I in part possess a plant growth-regulating action. They intervene in a regulating manner in the metabolism of the plant and can, therefore, be employed for selectively affecting materials contained in plants and for facilitating harvesting and for initiating desiccation and inhibition of growth.

The agents according to the invention can be applied in the customary formulations as wettable powders, emulsifiable concentrates, sprayable solutions, dusting agents, dressing agents, granules or microgranules.

Wettable powders are to be understood as meaning preparations which are uniformly dispersible in water and which, in addition to the active compound, also contain, as well as a diluent or inert material, if appropriate, wetting agents, for example polyoxyethylated alkylphenols, polyoxyethylated fatty alcohols, alkylsulfonates or alkylphenylsulfonates, and dispersing agents, for example sodium ligninsulfonate, sodium 2,2'-dinaphthylmethane-6,6'-disulfonate, sodium dibutylnaphthalenesulfonate or sodium oleoylmethyltauride. They are prepared in a customary manner, for example by grinding and mixing the components.

Emulsifiable concentrates can be prepared, for example, by dissolving the active compound in an inert organic solvent, for example butanol, cyclohexanone, dimethylformamide, xylene or higher-boiling aromatic solvents or hydrocarbons, with the addition of one or more emulsifiers. In the case of liquid active compounds, the solvent component can be omitted entirely or in part. The following are examples of emulsifiers which can be used: calcium alkylarylsulfonates, such as Ca dodecylbenzenesulfonate, or nonionic emulsifiers, such as polyglycol esters of fatty acids, alkylaryl polyglycol ethers, fatty alcohol polyglycol ethers, propylene oxide/ethylene oxide condensation products, alkyl polyglycol ethers, sorbitan esters of fatty acids, polyoxyethylenesorbitan esters of fatty acids or polyoxyethylenesorbitol esters.

Dusting agents are obtained by grinding the active compound with finely divided solid substances, for example talc, natural clays, such as kaolin, bentonite or pyrophillite, or diatomaceous earth.

Granules can be prepared either by atomizing the active compound onto adsorptive, granulated inert material or by applying concentrates of active compounds by means of binders, for example polyvinyl alcohol, sodium polyacrylate or mineral oils, to the surface of carriers, such as sand, kaolinite or granulated inert material. Suitable active compounds can also be granulated—if desired as a mixture with fertilizers—in the manner customary for the production of fertilizer granules.

In wettable powders, the concentration of active compound is about 10 to 90% by weight; the remainder up to 100% by weight consists of customary formulation ingredients. In emulsifiable concentrates, the concentration of active compound can be about 10 to 80% by weight. Formulations which can be applied as dusts in most cases contain 5 to 20% by weight of active compound, while sprayable solutions contain about 1 to 20% by weight. In the case of granules, the content of active compound depends in part on whether the active compound is in a liquid or solid form and on the granulating auxiliaries, fillers etc. which are used.

In addition, the said formulations of active compounds contain, if appropriate, the adhesives, wetting agents, dispersing agents, emulsifiers, penetration agents, solvents, fillers or carriers which are customary in a particular case.

For application, the concentrates present in a commercial form are, if appropriate, diluted in a customary manner, for example by means of water in the case of wettable powders, emulsifiable concentrates and dispersions and in part also in the case of microgranules. Formulations which are in the form of dusts and granules and also sprayable solutions are usually not diluted further with other inert substances before being used.

The application rates of the compounds of the formula I required when used as safeners can vary within wide limits depending on the indication and the herbicide used, and vary, in general, between 0.01 and 10 kg of active compound per hectare.

The following Examples serve to illustrate the invention.

A. FORMULATION EXAMPLES (a) A dusting agent is obtained by mixing 10 parts by weight of a compound of the formula I and 90 parts by weight of talc or an inert substance, and comminuting the mixture in a beaker mill.

(b) A wettable powder which is readily dispersible in water is obtained by mixing 25 parts by weight of a compound of the formula I, 64 parts by weight of kaolin-containing quartz as an inert substance, 10 parts by weight of potassium ligninsulfonate and 1 part by weight of sodium oleoylmethyltauride as a wetting and dispersing agent, and grinding the mixture in a pin disk mill.

(c) A dispersion concentrate which is readily dispersible in water is obtained by mixing 20 parts by weight of a compound of the formula I with 6 parts by weight of alkylphenol polyglycol ether (Triton X 207), 3 parts by weight of isotridecanol polyglycol ether (8 EO) and 71 parts by weight of paraffinic mineral oil (boiling range, for example, approx. 255 to over 377° C.), and grinding the mixture in a ball mill to a fineness of less than 5 microns.

(d) An emulsifiable concentrate is obtained from 15 parts by weight of a compound of the formula I, 75 parts by weight of cyclohexanone as solvent and 10 parts by weight of oxethylated nonylphenol as emulsifier.

(e) A concentrate composed of a phenoxycarboxylic acid ester and an antidote (10:1) and readily emulsifiable in water is obtained from 12.00% by weight of ethyl 2-[4-(6-chlorobenzoxazol-2-yl-oxy)-phenoxy]-propionate,
1.20% by weight of a compound of the formula I,
69.00% by weight of xylene,
7.80% by weight of calcium dodecylbenzenesulfonate,
6.00% by weight of ethoxylated nonylphenol (10 EO) and
4.00% by weight of ethoxylated castor oil (40 EO).

The formulation is carried out as indicated under Example (a).

(f) A concentrate composed of a phenoxycarboxylic acid ester and an antidote (1:10) and readily emulsifiable in water is obtained from 4.0% by weight of ethyl 2-[4-(6-chlorobenzoxazol-2-yl-oxy)-phenoxy]-propionate,
40.0% by weight of a compound of the formula I,
30.0% by weight of xylene,
20.0% by weight of cyclohexanone,
4.0% by weight of calcium dodecylbenzenesulfonate and
2.0% by weight of ethoxylated castor oil (40 EO).

B. CHEMICAL EXAMPLES

Precursors (1)Methyl α-chloro-α-(3-trifluoromethylphenylhydrazono)-glyoxylate 161.1 g (1.0 mole) of 3-trifluoromethylaniline were dissolved in a mixture of 400 ml of water and 326 ml of concentrated HCl, and 70 g of sodium nitrite in 400 ml of water were added dropwise at 0° C., with vigorous stirring.

The resulting diazonium salt solution was then added dropwise, with vigorous stirring, to a mixture, kept at +10° C., of 165.5 g of methyl α-chloroacetoacetate, 800 ml of water, 444 g of sodium acetate and 1,000 ml of ethanol. After being stirred for a further 3 hours, the mixture was diluted with water and the crude product was filtered off with suction and extracted by boiling with methanol.

Yield: 263.6 g=94%
Melting point: 145° C.

(2) Methylα-amino-α(3-trifluoromethylphenylhydrazono)-glyoxylate 100 g (0.356 mole) of methyl -chloro- -(3-trifluoromethylphenylhydrazono)-glyoxylate were dissolved in 560 ml of tetrahydrofuran, and 61 g of 25% strength aqueous ammonia were added dropwise at +15° to +20° C. After being stirred for a further 5 hours at room temperature, the mixture was poured into water, the product was filtered off with suction and the residue was extracted by boiling with methanol.

Yield: 88.3 g=95%
Melting point: 138° C.

End products (3) 1-(3-Trifluoromethylphenyl)-3-methoxycarbonyl-5-trichloromethyl-1,2,4-triazole (a) in toluene as solvent 26.1 g (0.1 mole) of methyl α-amino-α-(3-trifluoromethylphenylhydrazono)-glyoxylate in 150 ml of toluene were initially taken, 0.12 mole of trichloroacetyl chloride was added dropwise with stirring and the mixture was then boiled under reflux underneath a water separator until no further water passed over (approx. 1 hour).

After cooling, the toluene solution was washed with water, and the toluene was distilled off in vacuo. The crude product remaining was recrystallized from methanol.

Yield: 24 g=61.7%
Pale yellow crystals, melting point 92°-93° C.

(b) in tetrahydrofuran as solvent
182.8 g (0.7 mole) of methylα-amino-α-(3-trifluoromethylphenylhydrazono)-glyoxylate were dissolved in 1,200 ml of tetrahydrofuran, and, without cooling, 191 g (1.05 moles) of trichloroacetyl chloride were added dropwise in 10 minutes, with stirring. The mixture was stirred for 30 minutes at room temperature, then kept under reflux for 15 minutes and stirred for a further 5 hours at room temperature. The mixture was poured into water, and the precipi-tated crystals were filtered off with suction and washed with water. Yellowish crystals.

Yield: 233.8 g=86%
Melting point: 90° C.
After recrystallization from methanol, a sample melts at 92°-93° C.

(4) 1-(3-Trifluoromethylphenyl)-5-trichloromethyl-1,2,4-triazole-3-carboxylic acid 210 g (0.54 mole) of 1-(3-trifluoromethylphenyl)-3-methoxycarbonyl-5-trichloromethyl-1,2,4-triazole in 540 ml of methanol were initially taken, and 0.57 mole (22.8 g) of NaOH in 100 ml of water was added. After being stirred at room temperature for 5 hours, the mixture was poured into 4,000 ml of water, the undissolved substance was filtered off and the clear filtrate was adjusted to pH 1 with hydrochloric acid. Colorless crystals were precipitated and were filtered off with suction and washed with water. The substance which remained undissolved in water—the sodium salt of the carboxylic acid—was dissolved in a mixture of 2,000 ml of methanol and 1,000 ml of water, the pH of the solution was adjusted to 1 with hydrochloric acid, and the colorless crystalline precipitate was filtered off with suction and washed with water.

The combined fractions of the carboxylic acid were recrystallized from 1,000 ml of toluene.

Yield: 174 g=84%
Melting point: 133°-136° C.

(5) 1-(3-Trifluoromethylphenyl)-3-isopropoxycarbonyl-5-trichloromethyl-1,2,4-triazole 20 g (0.0534 mole) of 1-(3-trifluoromethylphenyl)-5-trichloromethyl-1,2,4-triazole-3-carboxylic acid in 70 ml of thionyl chloride were kept under reflux for 30 minutes, the excess thionyl chloride was removed in vacuo and the crude carboxylic acid chloride was boiled for 60 minutes in 120 ml of isopropanol. After the solution had cooled it was poured into ice water, and the colorless crystals were filtered off with suction.

The crude, colorless crystals were triturated at room temperature in a mixture of 1:2 methanol/water (50 ml) and were filtered off again with suction and dried in the air.

Yield: 19.4 g=87.3%
Melting point: 91° C.

(6)
1-(3-Trifluoromethylphenyl)-5-trichloromethyl-1,2,4-triazole-3-carboxylic acid 3'-trifluoromethylanilide 0.0345 mole of carboxylic acid were converted analogously to Example 5) into the acid chloride, the latter was dissolved in 80 ml of toluene, and a mixture of 0.0345 mole (5.56 g) of 3-trifluoromethylaniline and 0.0345 mole (3.5 g) of triethylamine was added dropwise at +5° C. in the course of 20 minutes. After being stirred at room temperature for 5 hours, the mixture was washed with water and the toluene was removed in vacuo. The residue was recrystallized from 40 ml of methanol. Colorless crystals, melting point 126° C.
Yield: 14.4 g=81%

(7)
1-(3-Trifluoromethylphenyl)-3-methoxycarbonyl-5-dichloromethyl-1,2,4-triazole 0.1 mole (26.1 g) of methyl α-amino-α-(3-trifluoromethylphenylhydrazono)-glyoxylate was dissolved in 150 ml of toluene, 0.105 mole (15.5 g) of dichloroacetyl chloride was added dropwise at room temperature, with stirring, and the mixture was kept under reflux underneath a water separator for 60 minutes. After cooling, the mixture was washed several times with water, and the toluene was removed in vacuo. The residue was a pale honey-colored syrup. $n_D^{30}$: 1.5259.
Yield: 28.2 g=80%
NMR spectrum in $CDCl_3$: $\underline{COOCH_3}$δ4.05; $\underline{CHCl_2}$δ6.72 Rf value in 2/1 toluene/ethyl acetate: 0.52.

(8)
1-(2,6-Diethylphenyl)-3-methoxycarbonyl-5-trichloromethyl-1,2,4-triazole 0.15 mole (37.4 g) of methyl-α-amino-α-(2,6-diethylphenylhydrazono)-glyoxylate was dissolved in 165 ml of tetrahydrofuran, and 0.194 mole (35.4 g) of trichloroacetyl chloride was added. After being stirred at room temperature for 3 hours the mixture was poured into water and thoroughly stirred with methylene chloride, the organic phase was washed with water, and the solvent was removed in vacuo.
Yield: 51.7 g=91.5%
Pale brown syrup which, according to the NMR spectrum and elementary analysis, is the open-chain compound

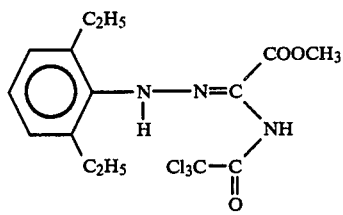

18.9 g (0.047 mole) of this compound in 120 ml of glacial acetic acid were kept under reflux for 1.5 hours; after cooling, the mixture was poured into water and thoroughly stirred with methylene chloride. The organic phase was washed three times with water, and the solvent was removed in vacuo.

The pale yellow crystals which remained were triturated with 20 ml of methanol and filtered off with suction.
Yield: 16.4 g=91%
Melting point: 76°-77° C.

(9)
1-(3-Trifluoromethylphenyl)-3-methoxycarbonyl-5-(2,2-dimethylethen-1-yl)-1,2,4-triazole 26.1 g (0.1 mole) of methyl α-amino-α-(3-trifluoromethylphenylhydrazono)-glyoxylate were dissolved in 150 ml of tetrahydrofuran, and 15.4 g (0.13 mole) of β,β-dimethylacrylyl chloride were added dropwise, without cooling, in the course of 10 minutes. After the reaction mixture had been boiled for one hour under reflux conditions, the bulk of the tetrahydrofuran was distilled off under normal pressure, and the reaction mixture was stirred with excess water. When the water had been decanted off, the crude crystals were recrystallized from methanol.
Yield: 24 g=73.7%
Melting point: 143°-144° C.

(10)
1-(4-Fluorophenyl)-3-methoxycarbonyl)-5-methoxymethyl-1,2,4-triazole 21.1 g (0.1 mole) of methyl α-amino-α-(4-fluorophenylhydrazono)-glyoxylate were dissolved in 140 ml of toluene, and 14.1 g (0.13 mole) of methoxyacetyl chloride were added dropwise, without cooling, in the course of 10 minutes. The toluene solution was boiled under a water separator for 1.5 hours, cooled and washed with twice 200 ml of water, the toluene was distilled off in vacuo and the residue was recrystallized from methanol.
Yield: 15.2 g=57.4%
Melting point: 93°-94° C.

(11)
1-(2,4-Dichlorophenyl)-3-ethoxycarbonyl-5-methyl-1,2,4-triazole:

(11a)
Diethylα-(2,4-dichlorophenylazo)-acetaminomalonate 0.2 mole (33.4 g) of 2,4-dichloroaniline was boiled for a short time in 60 ml of water and 75 ml of concentrated hydrochloric acid; the suspension was cooled to +5° C. and was diazotized at this temperature with 0.2 mole (13.8 g) of sodium nitrite in 25 ml of water.

The solution of the diazonium salt was added dropwise, in the course of 15 minutes and at +5° to 7° C., to a vigorously stirred mixture of 300 ml of ethanol, 200 ml of water, 100 g of sodium acetate and 0.2 mole (43.3 g) of diethyl acetaminomalonate. After being stirred for a further hour at room temperature, the mixture was poured into water, the product was filtered off with suction and the crystals were washed with water. After recrystallization from ethanol/water, the crystals melt at 123°-124° C.
Yield: 71 g=91%

(11b)
1-(2,4-Dichlorophenyl)-5-methyl-1,2,4-triazole-3-carboxylic acid 39 g (0.1 mole) of the product from Example 11a were boiled under reflux for 5 minutes in a mixture of 165 ml of water and 24.2 g of potassium hydroxide. The resulting clear solution was cooled to 60° C. and acidified with concentrated hydrochloric acid, and the 1-(2,4-dichlorophenyl)-5-methyl-1,2,4-triazole-3-carboxylic acid which had been precipitated was filtered off with suction and washed with water until it was neutral.

Yield: 25.6 g=94%
Melting point: 163°–164° C.

(11c)
1-(2,4-Dichlorophenyl)-3-ethoxycarbonyl-5-methyl-1,2,4-triazole 0.10 mole of (11b) was boiled under reflux in 150 ml of thionyl chloride for 2 hours, the excess thionyl chloride was removed in vacuo and the crude acid chloride in 500 ml of ethanol was heated at the boil for 30 minutes. The mixture was poured into water, and the precipitated crystals were filtered off with suction and washed with water until they were neutral.

Yield: 24 g=80%
Melting point: 131°–132° C.
After recrystallization from methanol, the crystals melt at 133°–134° C.

(12)
1-(2,4-Dichlorophenyl)-3-ethoxycarbonyl-5-methyl-1,2,4-triazole (12a) 0.1 mole (27.6 g) of ethyl α-amino-α-(2,4-dichlorophenylhydrazono)-glyoxylate in 150 ml of acetic anhydride was kept under reflux for 2 hours, the excess acetic anhydride was removed in vacuo and the crude product was recrystallized from ethanol.

Yield: 21.6 g=72%
Melting point: 133°–134° C.

(12b) 0.1 mole (27.6 g) of ethyl α-amino-α-(2,4-dichlorophenylhydrazono)-glyoxylate in 130 ml of triethyl orthoacetate was kept under reflux for 4 hours, the excess orthoester was removed in vacuo and the product was recrystallized from ethanol.

Yield: 18.9 g=63%
Melting point: 133°–134° C.

(13) 1-(2,4-Dichlorophenyl)-3-ethoxycarbonyl-1,2,4-triazole 0.1 mole (27.6 g) of ethyl α-amino- α-(2,4-dichlorophenylhydrazono)-glyoxylate in 120 ml of trimethyl orthoformate was kept under reflux for 5 hours, the excess orthoester was removed in vacuo and the residue was recrystallized from ethanol.

Yield: 21.4 g=75%
Melting point: 105°–106° C.

(14) 1-Phenyl-3-acetyl-5-trichloromethyl-1,2,4-triazole 23.6 g (0.13 mole) of trichloroacetyl chloride were added, all at once and with stirring, to 0.1 mole (17.7 g) of α-amino-α-phenylhydrazonomethylglyoxal in 150 ml of tetrahydrofuran. After being boiled under reflux for one hour, the mixture was poured into 1 liter of water, the water was decanted off from the precipitated crude product, and the latter was recrystallized from methanol.

Yield: 20.1 g=66%
Melting point: 139°–140° C.

The compounds of the formula I listed in Table I were prepared analogously to Preparation Examples 3 to 14.

TABLE I

| Example No. | $(Z)_n$ | Y | X | M.p. (°C.) $n_D^{30}$ | Preparation as in Example No. |
| --- | --- | --- | --- | --- | --- |
| 15 | 3-Cl | CCl$_3$ | —OC$_2$H$_5$ | 76–77 | 3a |
| 16 | 3-Cl | CCl$_3$ | —OH | 124–127 | 4 |
| 17 | 3-Cl | CHCl$_2$ | —OC$_2$H$_5$ | Syrup | 3a |
| 18 | 2-Cl | CCl$_3$ | —OC$_2$H$_5$ | 99–100 | 3a |
| 19 | 2-Cl | CCl$_3$ | —OH | 204–205 | 4 |
| 20 | 2-Cl | CCl$_3$ | —OCH$_3$ | 114–115 | 3b |
| 21 | 2-Cl | CCl$_3$ | —OCH$_2$CH$_2$CH$_3$ | 90–92 | 5 |
| 22 | 4-Cl | CHCl$_2$ | —OCH$_3$ | 152–153 | 3a |
| 23 | 3,5-Cl$_2$ | CHCl$_2$ | —OCH$_3$ | 1,5809 | 3a |
| 24 | 4-NO$_2$ | CHCl$_2$ | —OCH$_3$ | 149–150 | 3a |
| 25 | 3,5-Cl$_2$ | CCl$_3$ | —OCH$_3$ | 143–145 | 3b |
| 26 | 3,5-Cl$_2$ | CCl$_3$ | —OH | 194–195 | 4 |
| 27 | 2-Cl | CHCl$_2$ | —OC$_2$H$_5$ | 135–136 | 3a |
| 28 | 3-Cl | CHCl$_2$ | —OH | 114 | 4 |
| 29 | 2-Cl | CHCl$_2$ | —OCH$_3$ | 158 | 3a |
| 30 | 4-NO$_2$ | CCl$_3$ | —OCH$_3$ | 201–203 | 3b |
| 31 | H | CCl$_3$ | —OCH$_3$ | 103–104 | 3b |
| 32 | H | CCl$_3$ | —OH | 154–156 | 4 |
| 33 | 4-F | CHCl$_2$ | —OCH$_3$ | 168 | 3a |
| 34 | 3-CN | CCl$_3$ | —OH | 155 | 4 |
| 35 | 4-Cl—C$_6$H$_4$—O— | CCl$_3$ | —OH | 142 | 4 |
| 36 | 2,4-Cl$_2$ | CCl$_3$ | —OC$_2$H$_5$ | 111–112 | 8 |
| 37 | 2,4-Cl$_2$ | CCl$_3$ | —OH | 156 | 4 |
| 38 | 4-Cl—C$_6$H$_4$—O— | CCl$_3$ | —OCH$_3$ | 1,5925 | 3b |
| 39 | 2,4-Cl$_2$ | CHCl$_2$ | —OCH$_3$ | 147 | 3a |
| 40 | 2-Cl | CHCl$_2$ | —OH | 188–189 | 4 |

TABLE I-continued

| Example No. | (Z)$_n$ | Y | X | M.p. (°C.) $n_D^{30}$ | Preparation as in Example No. |
|---|---|---|---|---|---|
| 41 | 4-Cl, Cl (2-O—) | CCl$_3$ | —OCH$_3$ | syrup | 3b |
| 42 | 4-Cl, Cl (2-O—) | CCl$_3$ | —OH | 141 | 4 |
| 43 | 2,4-Cl$_2$ | CCl$_3$ | —NH—C$_6$H$_5$ | 215–217 | 6 |
| 44 | 2,4-Cl$_2$ | CCl$_3$ | —NH—C$_6$H$_4$—3-CF$_3$ | 166–167 | 6 |
| 45 | 3,5-Cl$_2$ | CCl$_3$ | " | 160–161 | 6 |
| 46 | 2,4-Cl$_2$, 5-OCH$_3$ | CCl$_3$ | " | 173 | 6 |
| 47 | 2,4-Cl$_2$ | CCl$_3$ | —OCH$_3$ | 162–163 | 3b |
| 48 | 2,4-Cl$_2$ | CCl$_3$ | —OCH$_2$CH$_2$CH$_2$CH$_3$ | 66–67 | 5 |
| 49 | 2-CH$_3$, 4-Cl | CCl$_3$ | —NH—C$_6$H$_4$-3-CF$_3$ | 166 | 6 |
| 50 | 2-CH$_3$, 4-Cl | CCl$_3$ | —NH—C$_6$H$_4$-3-OCH$_3$ | 167–168 | 6 |
| 51 | 2,4-Cl$_2$ | CCl$_3$ | —OCH$_2$—C(=O)—N(CH$_3$)—C$_6$H$_5$ | 187–188 | 5* |
| 52 | 3-CF$_3$ | CCl$_3$ | —OC$_2$H$_5$ | 64 | 3a |
| 53 | 3,5-Cl$_2$ | CCl$_3$ | —OCH$_2$—C(=O)—N(CH$_3$)—C$_6$H$_5$ | 203 | 5* |
| 54 | 2-CH$_3$, 4-Cl | CCl$_3$ | —NH—C$_6$H$_4$-2-Cl | 203 | 6 |
| 55 | 2,4-Cl$_2$ | CCl$_3$ | —NH—C$_6$H$_4$-4-OCH$_3$ | 193–194 | 6 |
| 56 | 2,4-Cl$_2$ | CCl$_3$ | —N(CH$_2$CH(CH$_3$))$_2$O (dimethylmorpholino) | 68–72 | 6 |
| 57 | 2,4-Cl$_2$ | CCl$_3$ | —NH—C$_6$H$_4$-4-CH$_3$ | 205–207 | 6 |
| 58 | 4-Cl | CCl$_3$ | —OCH$_3$ | 136–137 | 3b |
| 59 | 4-Cl | CCl$_3$ | —OH | 145–147 | 4 |

4,639,266

TABLE I-continued

| Example No. | (Z)$_n$ | Y | X | M.p. (°C.) $n_D^{30}$ | Preparation as in Example No. |
|---|---|---|---|---|---|
| 60 | 3-Cl, 4-F | CCl$_3$ | —O—⟨cyclohexyl-H⟩ | 131–132 | 5 |
| 61 | 3-Cl, 4-F | CCl$_3$ | —OCH$_2$CH(CH$_3$)$_2$ | 122–123 | 5 |
| 62 | 2,4-Cl$_2$ | CCl$_3$ | —NH—⟨2-Cl-phenyl⟩ | 160–163 | 6 |
| 63 | 2,4-Cl$_2$ | CCl$_3$ | —N(C$_2$H$_5$)$_2$ | glass-like | 6 |
| 64 | 4-CH$_3$ | CCl$_3$ | —OH | 146 | 4 |
| 65 | 4-CH$_3$ | CCl$_3$ | —OCH$_3$ | 132–134 | 3b |
| 66 | 4-F | CCl$_3$ | —OCH$_3$ | 113–114 | 3b |
| 67 | 2-CH$_3$, 4-Cl | CCl$_3$ | —OC$_2$H$_5$ | 117–118 | 8 |
| 68 | 2-CH$_3$, 4-Cl | CCl$_3$ | —OCH$_3$ | 125–126 | 3b |
| 69 | 3-CN | CCl$_3$ | —OCH$_3$ | 125–126 | 3b |
| 70 | 2,4-Cl$_2$ | CCl$_3$ | —OCH(CH$_3$)$_2$ | 154–155 | 5 |
| 71 | 2,4-Cl$_2$ | CCl$_3$ | —OCH$_2$CH$_2$CH$_3$ | 129–130 | 5 |
| 72 | 4-F | CCl$_3$ | —OH | 131–132 | 4 |
| 73 | 4-F | CCl$_3$ | —OCH$_2$CH$_2$CH$_3$ | 120–121 | 5 |
| 74 | 3-Cl, 4-F | CCl$_3$ | —OCH$_3$ | 114–115 | 3b |
| 75 | 2,6-(C$_2$H$_5$)$_2$ | CCl$_3$ | —OH | 193–195 | 4 |
| 76 | 2,4-Cl$_2$ | CCl$_3$ | —OCH$_2$CH(CH$_3$)$_2$ | 119–121 | 5 |
| 77 | 2-Cl | CCl$_3$ | —OCH(CH$_3$)$_2$ | 131–132 | 5 |
| 78 | 2,4-Cl$_2$, 5-OCH$_3$ | CCl$_3$ | —OCH$_3$ | 155 | 3b |
| 79 | 2,4-Cl$_2$, 5-OCH$_3$ | CCl$_3$ | —OH | 215 | 4 |
| 80 | 2-CH$_3$, 4-Cl | CCl$_3$ | —OH | 112 | 4 |
| 81 | 2-Cl | CCl$_3$ | —OCH$_2$CH(CH$_3$)$_2$ | 79–80 | 5 |
| 82 | 2-CH$_3$, 4-Cl | CCl$_3$ | —OCH$_2$—C(=O)—N(CH$_3$)—C$_6$H$_5$ | 153 | 5* |
| 83 | 3-Cl, 4-F | CCl$_3$ | —OC$_2$H$_5$ | 118–119 | 8 |
| 84 | 3-Cl, 4-F | CCl$_3$ | —OH | 174 | 4 |
| 85 | 4-F | CCl$_3$ | —OCH$_2$CH(CH$_3$)$_2$ | 103–104 | 5 |
| 86 | 2-CH$_3$, 4-Cl | CCl$_3$ | —OCH$_2$CH$_2$CH$_2$CH$_3$ | 112 | 5 |
| 87 | 4-Cl | CCl$_3$ | —OC$_2$H$_5$ | 161–162 | 8 |
| 88 | 4-CH$_3$ | CCl$_3$ | —OCH(CH$_3$)$_2$ | 154–155 | 5 |
| 89 | H | CHCl$_2$ | —OH | 185 | 4 |
| 90 | 2,4-Cl$_2$ | CF$_3$ | —OCH$_3$ | 131 | 3b |
| 91 | 4-CH$_3$ | CCl$_3$ | —OC$_2$H$_5$ | 104–105 | 8 |
| 92 | 4-CH$_3$ | CCl$_3$ | —OCH$_2$CH(CH$_3$)$_2$ | 125–126 | 5 |
| 93 | 4-Cl, 2-Cl-phenyl-O— | CCl$_3$ | —OC$_2$H$_5$ | 147 | 8 |
| 94 | " | CCl$_3$ | —OCH$_2$CH$_2$CH$_3$ | 99 | 5 |
| 95 | 4-F | CF$_3$ | —OCH$_3$ | 87–88 | 3b |
| 96 | 4-Cl | CCl$_3$ | —OCH$_2$CH(CH$_3$)$_2$ | 138–139 | 5 |
| 97 | 2,6-(C$_2$H$_5$)$_2$ | CCl$_3$ | —OC$_2$H$_5$ | 96–97 | 8 |
| 98 | 3,4-Cl$_2$ | CCl$_3$ | —OCH$_3$ | 133 | 3b |
| 99 | 2,6 (C$_2$H$_5$)$_2$ | CCl$_3$ | —ONa | 233–234 | 4 |
| 100 | 2,6 (C$_2$H$_5$)$_2$ | CCl$_3$ | —OCH$_2$CH$_2$CH$_3$ | 1.5390 | 5 |
| 101 | 2,6 (C$_2$H$_5$)$_2$ | CCl$_3$ | —OCH(CH$_3$)$_2$ | 83–84 | 5 |
| 102 | 2,6 (C$_2$H$_5$)$_2$ | CCl$_3$ | —OCH$_2$CH(CH$_3$)$_2$ | 1,5147 | 5 |
| 103 | 3,4-Cl$_2$ | CCl$_3$ | OH | 167–168 | 4 |
| 104 | 2-CF$_3$, 4-Cl | CCl$_3$ | OCH$_3$ | 110 | 3a |
| 105 | 2-CF$_3$, 4-Cl | CCl$_3$ | OH | 143–145 | 4 |
| 106 | 2-F, 4-Cl—5-OCH$_3$ | CCl$_3$ | OCH$_3$ | 177–178 | 3a |
| 107 | 2-F, 4-Cl, 5-OCH$_3$ | CCl$_3$ | OH | 176 | 4 |
| 108 | 2-CHF$_2$CF$_2$O— | CCl$_3$ | OCH$_3$ | 116–117 | 3a |
| 109 | 3-CHClF—CF$_2$O— | CCl$_3$ | OCH$_3$ | syrup | 3a |
| 110 | 2-CH$_3$, 3-Cl | CCl$_3$ | OCH$_3$ | 144–145 | 3a |
| 111 | 2,6-Cl$_2$ | CCl$_3$ | OCH$_3$ | 143–144 | 3a |
| 112 | 2,5-(OCH$_3$)$_2$, 4-Cl | CCl$_3$ | OCH$_3$ | 149 | 3a |
| 113 | 2,5-(OCH$_3$)$_2$, 4-Cl | CCl$_3$ | OH | 223–224 | 4 |

TABLE I-continued

| Example No. | $(Z)_n$ | Y | X | M.p. (°C.) $n_D^{30}$ | Preparation as in Example No. |
|---|---|---|---|---|---|
| 114 | 3,5-Cl$_2$, 4-OCH$_3$ | CCl$_3$ | OCH$_3$ | 148–149 | 3a |
| 115 | 3,5-Cl$_2$—4-OCH$_3$ | CCl$_3$ | OH | 150 | 4 |
| 116 | 2-Cl, 4-Br | CCl$_3$ | OC$_2$H$_5$ | 113–114 | 3a |
| 117 | 2-Cl, 4-Br | CCl$_3$ | OH | 220 | 4 |
| 118 | 2-Br | CCl$_3$ | OCH$_3$ | 126–127 | 3a |
| 119 | 2-Br | CCl$_3$ | OH | 195–196 | 4 |
| 120 | 2,4-Cl$_2$ | CCl$_3$ | OCH$_2$CH$_2$Cl | 88–89 | 5 |
| 121 | 3-CHClF—CF$_2$O— | CCl$_3$ | OH | 128–130 | 4 |
| 122 | 2-CH$_3$, 4-Cl | CCl$_3$ | CH$_3$ | 141 | 14 |
| 123 | 3-CH$_3$, 4-CHF$_2$CF$_2$O | CCl$_3$ | CH$_3$ | 119–120 | 14 |
| 124 | 2,4-Cl$_2$ | CCl$_3$ | CH$_3$ | 120–121 | 14 |
| 125 | 3-OCF$_3$ | CCl$_3$ | CH$_3$ | 92–93 | 14 |
| 126 | 3-CHCl$_2$CF$_2$O | CCl$_3$ | CH$_3$ | 114–115 | 14 |
| 127 | H | CCl$_3$ | CH$_3$ | 139–140 | 14 |
| 128 | 2-Cl | CCl$_3$ | CH$_3$ | 121–122 | 14 |
| 129 | 3-CF$_2$Cl | CCl$_3$ | CH$_3$ | syrup | 14 |
| 130 | 4-Cl | (CH$_3$)$_2$C=CH— | OCH$_3$ | 118–119 | 9 |
| 131 | 2-CH$_3$, 4-Cl | (CH$_3$)$_2$C=CH— | OCH$_3$ | 142–143 | 9 |
| 132 | 2-Cl | CH$_2$Cl | OCH$_3$ | 112–113 | 10 |
| 133 | 2-CH$_3$, 4-Cl | CH$_3$ | OCH$_3$ | 73 | 10 |
| 134 | 3-Cl, 4-F | (CH$_3$)$_2$C=CH— | OCH$_3$ | 185–186 | 9 |
| 135 | 2,4-Cl$_2$, 5-OCH$_3$ | (CH$_3$)$_2$C=CH— | OCH$_3$ | 200–201 | 9 |
| 136 | 3,4-Cl$_2$ | CHCl$_2$—CF$_2$— | OC$_2$H$_5$ | $n_D^{30}$: 1.5458 | 9 |
| 137 | 2-CH$_3$, 4-Cl | CHCl$_2$—CF$_2$— | OC$_2$H$_5$ | $n_D^{30}$: 1.5272 | 9 |
| 138 | 2-CH$_3$, 4-Cl | CHF$_2$—CF$_2$— | OC$_2$H$_5$ | $n_D^{30}$: 1.4991 | 9 |
| 139 | 4-F | CHF$_2$—CF$_2$— | OCH$_3$ | 66–67 | 9 |
| 140 | 2-Cl | (CH$_3$)$_2$C=CH— | OH | 194 | 4 |
| 141 | 3,4-Cl$_2$ | CF$_2$H—CF$_2$— | OC$_2$H$_5$ | $n_D^{30}$: 1.5198 | 9 |
| 142 | 2,4-Cl$_2$, 5-OCH$_3$ | CF$_2$H—CF$_2$— | OCH$_3$ | 112–113 | 9 |
| 143 | 2-CH$_3$, 4-Cl | CH$_3$CH=CH— | OCH$_3$ | 175–176 | 9 |
| 144 | 4-F | 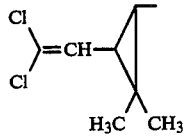 | OCH$_3$ | 149–160 | 9 |
| 145 | 3-CF$_3$ | HCF$_2$—CF$_2$— | OCH$_3$ | syrup | 9 |
| 146 | 2,4-Cl$_2$ | HCF$_2$—CF$_2$— | OC$_2$H$_5$ | syrup | 9 |
| 147 | 2,4-Cl$_2$ | HCF$_2$—(CF$_2$)$_3$— | OC$_2$H$_5$ | 115–116 | 9 |
| 148 | 2,4-Cl$_2$ | BrCF$_2$—CF$_2$— | OC$_2$H$_5$ | 100–101 | 9 |
| 149 | 2,4-Cl$_2$ | HCF$_2$—CF$_2$— | OH | 123–124 | 9 |
| 150 | 2-Cl | CH$_3$ | OH | 190 | 11b |
| 151 | 2-Cl | CH$_3$ | OC$_2$H$_5$ | 110–111 | 11c |
| 152 | 4-Cl | CH$_3$ | OH | 172 | 11b |
| 153 | 4-Cl | CH$_3$ | OC$_2$H$_5$ | 115 | 11c |
| 154 | 3-Cl, 4-F | CH$_3$ | OH | 183 | 11b |
| 155 | 4-F | CH$_3$ | OH | 177 | 11b |
| 156 | 2-CH$_3$, 4-Cl | CH$_3$ | OH | 177–178 | 11b |
| 157 | 2,4-Cl$_2$, 5-OCH$_3$ | CH$_3$ | OH | 193–194 | 11b |
| 158 | 2,4-Cl$_2$ | CH$_3$ | OCH$_3$ | 180–181 | 11c |
| 159 | 3-Cl, 4-F | CH$_3$ | OCH$_3$ | 140–142 | 11c |
| 160 | 3-Cl, 4-F | CH$_3$ | OC$_2$H$_5$ | 114–115 | 11c |
| 161 | 2,6-(C$_2$H$_5$)$_2$ | CHF$_2$—CF$_2$— | OH | 222–223 | 4 |
| 162 | 4-F | CH$_3$ | OC$_2$H$_5$ | 105–106 | 11c |
| 163 | 2-CH$_3$, 4-Cl | CH$_3$ | OC$_2$H$_5$ | 153–154 | 11c |
| 164 | 2,4-Cl$_2$ | H | OH | 185–186 | 4 |
| 165 | 2,4-Cl$_2$ | H | OC$_2$H$_5$ | 105–106 | 13 |
| 166 | 4-CH$_3$ | CH$_3$ | OC$_2$H$_5$ | 1,5466 | 11c |
| 167 | 4-CH$_3$ | CH$_3$ | OH | 183 | 11b |
| 168 | 2-Cl, 4-Br | CH$_3$ | OC$_2$H$_5$ | 142–143 | 11c |
| 169 | 2-Cl, 4-Br | CH$_3$ | OH | 172–173 | 11b |
| 170 | 3-CF$_3$ | CH$_3$ | OH | 164–165 | 11b |
| 171 | 2,4-Cl$_2$ | CH$_3$ | OC$_2$H$_5$ | 133–134 | 11c |
| 172 | 2,4-Cl$_2$ | CH$_3$ | OH | 163–164 | 11b |

*in toluene, using an equimolar amount of the alcohol, and triethylamine as an acid-binder.

C. BIOLOGICAL EXAMPLES

Example 1

Wheat was grown in pots of diameter 9 cm in a greenhouse until it had reached the 3-leaf to 4-leaf stage, and was then treated with the herbicide and the compounds according to the invention. The herbicides and the compounds of the formula I were applied in the form of aqueous suspensions or emulsions, applying an amount of water equivalent to 800 liters/hectare. 3 weeks after the treatment, the plants were assessed for any kind of damage caused by the herbicides applied, particular account being taken of the extent of long-lasting inhibition of growth.

The results in Table 1 illustrate that the compounds according to the invention can reduce severe herbicidal damage very effectively.

Even in the case of considerable overdosages of the herbicide H of 2.0 kg of active substance per hectare, the herbicidal damage symptoms which occurred are greatly reduced, so that only slight permanent damage remains. This illustrates the good safener action. Slight damage is, of course, completely eliminated (see Example 2). Mixtures of herbicides and compounds according to the invention are thus suitable for selectively combating weeds in cereals.

TABLE 1

| Compounds H + | Example No. | Dose, kg of a.i. per hectare | Herbicidal action, % TA |
|---|---|---|---|
| H | — | 2,0 | 75 |
| H + | 17 | 2.0 + 2.5 | 20 |
| H + | 22 | " | 30 |
| H + | 7 | " | 30 |
| H + | 27 | " | 25 |
| H + | 15 | " | 11 |
| H + | 16 | " | 24 |
| H + | 36 | " | 13 |
| H + | 67 | " | 10 |
| H + | 25 | " | 25 |
| H + | 78 | " | 18 |
| H + | 31 | " | 20 |
| H + | 69 | " | 28 |
| H + | 3 | " | 26 |
| H + | 79 | " | 30 |
| H + | 80 | " | 30 |
| H + | 32 | " | 24 |
| H + | 37 | " | 24 |
| H + | 19 | " | 25 |
| H + | 43 | " | 30 |
| H + | 63 | " | 20 |
| H + | 18 | " | 13 |
| H + | 29 | " | 20 |
| H + | 33 | " | 20 |
| H + | 39 | " | 20 |
| H + | 41 | " | 20 |
| H + | 64 | " | 20 |
| H + | 66 | " | 15 |
| H + | 73 | " | 25 |
| H + | 85 | " | 20 |
| H + | 74 | " | 25 |
| H + | 127 | 2.0 + 1.0 | 30 |
| H + | 89 | 2.0 + 2.5 | 30 |
| H + | 90 | " | 50 |
| H + | 146 | " | 30 |
| H + | 9 | " | 40 |
| H + | 160 | " | 60 |
| H + | 163 | " | 30 |
| H + | 20 | " | 13 |
| H + | 21 | " | 22 |
| H + | 47 | " | 22 |
| H + | 48 | " | 7 |
| H + | 70 | " | 10 |
| H + | 71 | " | 50 |
| H + | 76 | " | 20 |
| H + | 68 | " | 10 |
| H + | 72 | " | 22 |
| H + | 73 | " | 40 |
| H + | 84 | " | 35 |
| H + | 8 | " | 30 |
| H + | 75 | " | 50 |
| H + | 59 | " | 20 |
| H + | 83 | " | 28 |
| H + | 52 | " | 60 |
| H + | 5 | " | 22 |
| H + | 77 | " | 20 |
| H + | 81 | " | 30 |
| H + | 92 | " | 40 |
| H + | 91 | " | 40 |

TABLE 1-continued

| Compounds H + | Example No. | Dose, kg of a.i. per hectare | Herbicidal action, % TA |
|---|---|---|---|
| H + | 88 | " | 50 |
| H + | 86 | " | 40 |
| H + | 87 | " | 20 |
| H + | 96 | " | 40 |
| H + | 100 | " | 40 |
| H + | 103 | " | 30 |
| H + | 102 | " | 40 |
| H + | 104 | 2.0 + 2.5 | 50 |
| H + | 106 | " | 50 |
| H + | 107 | " | 50 |
| H + | 110 | " | 48 |
| H + | 111 | " | 50 |
| H + | 116 | " | 20 |
| H + | 118 | " | 30 |
| H + | 113 | " | 60 |
| H + | 115 | " | 40 |
| H + | 117 | " | 18 |
| H + | 119 | " | 50 |
| H + | 120 | " | 20 |
| H + | 137 | " | 25 |
| H + | 138 | " | 25 |
| H + | 139 | " | 25 |
| H + | 141 | " | 40 |
| H + | 142 | " | 30 |
| H + | 143 | " | 40 |
| H + | 133 | " | 50 |
| H + | 134 | " | 50 |
| H + | 135 | " | 50 |
| H + | 148 | " | 20 |
| H + | 149 | " | 55 |
| H + | 11c | " | 40 |
| H + | 11b | " | 25 |
| H + | 150 | " | 35 |
| H + | 151 | " | 30 |
| H + | 152 | " | 50 |
| H + | 153 | " | 27 |
| H + | 154 | " | 27 |
| H + | 155 | " | 50 |
| H + | 156 | " | 25 |
| H + | 157 | " | 43 |
| H + | 158 | " | 20 |
| H + | 171 | " | 20 |

Abbreviations in Table 1
TA = Triticum aestivum
a.i. = active ingredient
H = fenoxaprop-ethyl = ethyl 2-(4-(6-chlorobenzoxazol-2-yloxy)-phenoxy)-propionate Example 2

Wheat and the two gramineous weeds *Alopecurus myosuroides* and *Avena fatua* were sown in loamy sandy soil in pots of diameter 9 cm, were cultivated in a greenhouse under cool conditions until tillering began and were treated with the compounds according to the invention. The preparations were applied in the form of aqueous emulsions or suspensions, together with the herbicide (tank mix), with a water application rate of 300 liters/hectare.

4 weeks after application, the test plants were assessed for alterations in growth and damage.

The results in Table 2 show that the compounds according to the invention have a very good safener property and can effectively prevent herbicidal damage which takes place on crop plants such as, for example, cereals, without impairing the actual herbicidal action against gramineous weeds.

Mixtures of herbicides and compounds according to the invention can thus be employed for selectively combating weeds.

TABLE 2

| Herbicide H + | Compound from Example No. | Dose, kg of active ingredient per hectare H + Compound from Example No. | % damage on wheat (TA) | % herbicidal action against ALM | % herbicidal action against AVF |
|---|---|---|---|---|---|
| Herbicide H | — | 0.8 | 52 | — | — |
|  |  | 0.4 | 40 | 100 | 100 |
|  |  | 0.2 | 18 | 98 | 100 |
| H + | 7 | 0.8 + 0.4 | 2 | — | — |
|  |  | 0.4 + 0.2 | 0 | 100 | 100 |
|  |  | 0.2 + 0.1 | 0 | 98 | 100 |
| H + | 27 | 0.8 + 0.4 | 2 | — | — |
|  |  | 0.4 + 0.2 | 0 | 100 | 100 |
|  |  | 0.2 + 0.1 | 0 | 99 | 99 |
| H + | 15 | 0.8 + 0.4 | 2 | — | — |
|  |  | 0.4 + 0.2 | 0 | 100 | 100 |
|  |  | 0.2 + 0.1 | 0 | 100 | — |
| H + | 16 | 0.8 + 0.4 | 1 | — | — |
|  |  | 0.4 + 0.2 | 0 | 100 | 100 |
|  |  | 0.2 + 0.1 | 0 | 98 | 98 |
| H + | 18 | 0.8 + 0.4 | 3 | — | — |
|  |  | 0.4 + 0.2 | 0 | 100 | 100 |
|  |  | 0.2 + 0.1 | 0 | 100 | 97 |
| H + | 37 | 0.8 + 0.4 | 2 | — | — |
|  |  | 0.4 + 0.2 | 0 | 100 | 100 |
|  |  | 0.2 + 0.1 | 0 | 99 | 100 |
| H + | 36 | 0.8 + 0.4 | 2 | — | — |
|  |  | 0.4 + 0.2 | 0 | 100 | 100 |
|  |  | 0.2 + 0.1 | 0 | 97 | 100 |
| H + | 78 | 0.8 + 0.4 | 2 | — | — |
|  |  | 0.4 + 0.2 | 0 | 100 | 100 |
|  |  | 0.2 + 0.1 | 0 | 100 | 100 |
| H + | 67 | 0.8 + 0.4 | 2 | — | — |
|  |  | 0.4 + 0.2 | 0 | 100 | 100 |
|  |  | 0.2 + 0.1 | 0 | 100 | 100 |
| H + | 22 | 0.8 + 0.4 | 2 | — | — |
|  |  | 0.4 + 0.2 | 0 | 100 | 100 |
|  |  | 0.2 + 0.1 | 0 | 100 | 99 |
| H + | 79 | 0.8 + 0.4 | 3 | — | — |
|  |  | 0.4 + 0.2 | 2 | 100 | 100 |
|  |  | 0.2 + 0.1 | 0 | 98 | 98 |
| H + | 80 | 0.8 + 0.4 | 4 | — | — |
|  |  | 0.4 + 0.2 | 2 | 100 | 100 |
|  |  | 0.2 + 0.1 | 0 | 98 | 100 |
| H + | 63 | 0.8 + 0.4 | 0 | — | — |
|  |  | 0.4 + 0.2 | 0 | 100 | 100 |
|  |  | 0.2 + 0.1 | 0 | 99 | 97 |
| H + | 19 | 0.8 + 0.4 | 2 | — | — |
|  |  | 0.4 + 0.2 | 0 | 100 | 100 |
|  |  | 0.2 + 0.1 | 0 | 100 | 97 |

ALM = *Alopecurus myosuroides*
AVF = *Avena fatua*
H = see Table 1

Example 3

Barley (variety Oriol) was sown in loamy sandy soil in pots of diameter 13 cm and was cultivated under outdoor climatic conditions until tillering began, and was treated with the mixtures (tank mix) of the herbicide and the compounds according to the invention. The preparations were applied in the form of aqueous emulsions or suspensions, with a water application rate of 300 liters/hectare.

2 weeks after application, the test plants were assessed for alterations in growth and other damage.

As the results in Table 3 show, the compounds according to the invention have very good safener properties and can thus effectively prevent herbicidal damage occurring on crop plants such as, for example, barley, without impairing the actual success of combating the gramineous weeds.

TABLE 3

| Compound $H_1$ + Example No. | Dosage (kg of a.i. per hectare) | Herbicidal action, % HV |
|---|---|---|
| $H_1$ | 3.0 | 30 |
|  | 1.5 | 13 |
| $H_1$ + 36 | 3.0 + 0.3 | 15 |
|  | 1.5 + 0.15 | 3 |

Abbreviations:
HV = *Hordeum vulgare*
$H_1$ = Diclofop-methyl [methyl 2-(4-(2,4-dichlorophenoxy)-phenoxy)-propionate]

We claim:

1. A plant protection agent which contains an effective amount of a compound of the formula I

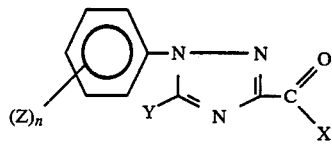
(I)

in which
  the Zs are identical or different and denote halogen, nitro, cyano, trifluoromethyl, ($C_1$–$C_4$)-alkyl, ($C_1$–$C_4$)-alkoxy or ($C_1$–$C_4$)-alkylthio, it being possible for the alkyl, alkoxy and alkylthio groups to be substituted by one or more halogen atoms, in particular fluorine or chlorine, or ($C_3$–$C_6$)-cycloalkyl which can be substituted by ($C_1$–$C_4$)-alkyl, or denotes phenyl or phenoxy, it being possible for phenyl and phenoxy to be monosubstituted or polysubstituted by halogen and/or monosubstituted by trifluoromethyl,
  Y denotes hydrogen, ($C_1$–$C_4$)-alkyl which can be wholly or partially substituted by halogen atoms and/or monosubstituted by ($C_1$–$C_4$)-alkoxy or ($C_1$–$C_4$)-alkylthio, or ($C_2$–$C_6$)-alkenyl or $C_2$–$C_6$)-alkinyl or denotes (($C_3$–$C_6$)-cycloalkyl which can be substituted by ($C_1$–$C_4$)-alkyl and/or a dichlorovinyl radical, and
  X denotes hydroxyl, ($C_1$–$C_4$)-alkyl, (($C_3$–$C_6$)-cycloalkoxy, phenyl-($C_1$–$C_6$)-alkoxy, phenoxy, ($C_2$–$C_6$)-alkenyloxy, ($C_2$–$C_6$)-alkinyloxy or ($C_1$–$C_6$)-alkoxy or ($C_1$–$C_6$)-alkylthio, it being possible for the alkoxy or alkylthio group to be substituted by ($C_1$–$C_2$)-alkoxy, mono-($C_1$–$C_4$)-alkylaminocarbonyl, di-[($C_1$–$C_4$-alkyl]aminocarbonyl, phenylaminocarbonyl, N-[($C_1$–$C_4$-alkyl]-N-phenyl-aminocarbonyl, mono-($C_1$–$C_6$)-alkylamino, di-($C_1$–$C_6$)-alkylamino, ($C_1$–$C_6$-alkylcarbonyloxy, ($C_1$–$C_2$)-alkylthio, cyano or halogen, or denotes a radical of the formulae

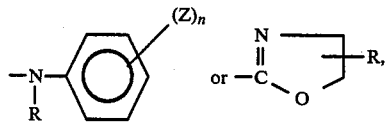

in which R in each case denotes hydrogen or ($C_1$–$C_4$)-alkyl, or denotes mono-($C_1$–$C_4$)-alkylamino, di-($C_1$–$C_4$)-alkylamino, ($C_5$–$C_6$)-cycloalkylamino, piperidino, morpholino or 2,6-dimethylmorpholino or a radical of the formula

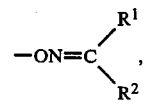

in which $R^1$ and $R^2$ can be identical or different and denote ($C_1$–$C_4$)-alkyl radicals, and in which $R^1$ and $R^2$ together can also form a 5-membered, 6-membered or 7-membered cycloalkyl radical, and
  n denotes the number 0, 1, 2 or 3, or, in the event that X=OH, salts thereof which can be employed for agriculture.

2. An agent as claimed in claim 1, which contains a compound of the formula I of claim 1 in which Y denotes ($C_1$–$C_2$)-alkyl which can be wholly or partially substituted by F, Cl or Br,
the Zs are identical or different and denote halogen, ($C_1$–$C_4$)-alkoxy, ($C_1$–$C_4$)-alkyl or $CF_3$,
X denotes ($C_1$–$C_6$)-alkoxy or hydroxyl and n denotes 1, 2 or 3.

3. An agent as claimed in claim 2, wherein Y denotes $CCl_3$, $CHCl_2$, $CHF_2CF_2$ or $CH_3$.

4. An agent as claimed in claim 1 which, in combination with a compound of the formula I of claims 1, 2, or 3, additionally contain a herbicide from the group comprising thiolcarbamates, carbamates, halogenoacetanilides, phenoxy-, naphthoxy-, phenoxy-phenoxy or heteroaryloxphenoxy-carboxylic acid esters or dimedone oxime derivatives, said compound and said herbicide being present in a ratio which is effective to reduce the phytotoxic side-effects of the herbicide.

5. A process for protecting crop plants against the phytotoxic side-effects of herbicides, which comprises treating the plants, plant seeds or cultivated areas with an effective amount of a compound of the formula I of claim 1, before, after or at the same time as the herbicide.

6. The process as claimed in claim 5, wherein the herbicide employed is a thiolcarbamate, carbamate, halogenoacetanilide, phenoxy-, naphthoxy-, phenoxyphenoxy- or heteroaryloxyphenoxy-carboxylic acid ester or a dimedone oxime derivative.

7. A compound of the formula I

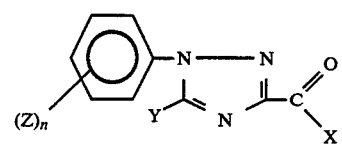
(I)

in which
  the Zs are identical or different and denote halogen, nitro, cyano, trifluoromethyl, ($C_1$–$C_4$)-alkyl, ($C_1$–$C_4$)-alkoxy or ($C_1$–$C_4$)-alkylthio, it being possible for the alkyl, alkoxy and alkylthio groups to be substituted by one or more halogen atoms, in particular fluorine or chlorine, or ($C_3$–$C_6$)-cycloalkyl which can be substituted by ($C_1$–$C_4$)-alkyl, or denotes phenyl or phenoxy, it being possible for phenyl and phenoxy to be monosubstituted or polysubstituted by halogen and/or monosubstituted by trifluoromethyl,
  Y denotes hydrogen, ($C_1$–$C_4$)-alkyl which can be wholly or partially substituted by halogen atoms and/or monosubstituted by ($C_1$–$C_4$)-alkoxy or ($C_1$–$C_4$)-alkylthio, or ($C_2$–$C_6$)-alkenyl or ($C_2$–$C_6$)-alkinyl or denotes ($C_3$–$C_6$)-cycloalkyl which can be substituted by ($C_1$–$C_4$)-alkyl and/or a dichlorovinyl radical, and
  X denotes hydroxyl, ($C_1$–$C_4$)-alkyl, ($C_3$–$C_6$)-cycloalkoxy, phenyl- $C_1$–$C_6$)-alkoxy, phenoxy, ($C_2$–$C_6$)-alkenyloxy, ($C_2$–$C_6$)-alkinyloxy or ($C_1$–$C_6$)-alkoxy or ($C_1$–$C_6$)-alkylthio, it being possible for the alkoxy or alkylthio group to be substituted by ($C_1$–$C_2$)-alkoxy, mono-($C_1$–$C_4$)-alkylaminocarbonyl, di-[($C_1$–$C_4$)-alkyl]aminocarbonyl, phenylaminocarbonyl, N-[($C_1$–$C_4$)-alkyl]-N-phenyl-aminocarbonyl, mono-($C_1$–$C_6$)-alkylamino, di-($C_1$–$C_6$)-alkylamino, ($C_1$–$C_6$-alkyl)- carbonyloxy, $(C_1-C_2)$-alkylthio, cyano or halogen, or denotes a radical of the formulae

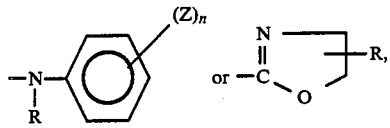

in which R in each case denotes hydrogen or $(C_1-C_4)$-alkyl, or denotes mono-$(C_1-C_4)$-alkylamino, di-$(C_1-C_4)$-alkylamino, $(C_5-C_6)$-cycloalkylamino, piperidino, morpholino or 2,6-dimethylmorpholino or a radical of the formula

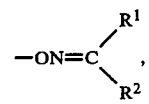

in which $R^1$ and $R^2$ can be identical or different and denote $(C_1-C_4)$-alkyl radicals, and in which $R^1$ and $R^2$ together can also form a 5-membered, 6-membered or 7-membered cycloalkyl radical, and n denotes the number 0, 1, 2, or 3, or, in the event that x=OH, salts thereof which can be employed for agriculture, it being necessary, in the event that $X=(C_1-C_4)$-alkyl, for Y to denote $CCl_3$ or $CHCl_2$, and excepting the compounds of the formula I in which (a) Y denotes H, $(Z)_n$ denotes H, 4-Cl, 4—$CH_3$, —$OCH_3$ or 4-$OC_2H_5$ and X denotes -$CH_3OH$, $OCH_3$ or $OC_2H_5$, (b) Y denotes $CH_3$, $(Z)_n$ denotes H4-$NO_2$, 4-$OCH_3$, 2-Cl, 4-Cl, 2-$OCH_3$-4-$NO_2$ or 2-$CH_3$-4-$NO_2$ and X denotes OH or $OC_2H_5$ and (c) Y denotes $C_2H_5$ or $CH(CH_3)_2$, $(Z)_n$ denotes H and X denotes $OCH_3$.

* * * * *